United States Patent [19]

Iizuka et al.

[11] Patent Number: 4,632,934

[45] Date of Patent: Dec. 30, 1986

[54] IMIDAZOLE DERIVATIVES AND PHARMACEUTICAL USE THEREOF

[75] Inventors: Kinji Iizuka; Keniji Akahane; Denichi Momose; Yukio Kamijo; Yukiyoshi Ajisawa, all of Nagano, Japan

[73] Assignees: Kissei Pharmaceutical Co., Ltd.; Ono Pharmaceutical Co., Ltd., both of Japan

[21] Appl. No.: 68,365

[22] Filed: Aug. 21, 1979

[30] Foreign Application Priority Data

Aug. 21, 1978 [JP] Japan .................................. 53-101549

[51] Int. Cl.⁴ .................. C07D 233/54; A61K 31/415
[52] U.S. Cl. ...................................... 514/399; 548/341
[58] Field of Search .................... 548/341; 424/273 R; 542/414, 413; 514/399

[56] References Cited

U.S. PATENT DOCUMENTS 4,017,631  4/1977  Janssen et al. ........................ 548/341
4,101,665  7/1978  Heeres ................................. 548/341

Primary Examiner—Henry R. Jiles
Assistant Examiner—Robert C. Whittenbaugh
Attorney, Agent, or Firm—Sughrue, Mion, Zinn, Macpeak, and Seas

[57] ABSTRACT

The imidazole derivatives of the formula:

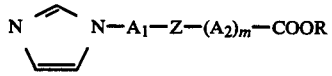

wherein R is a hydrogen atom or an alkyl group, $A_1$ and $A_2$, which may be the same or different, each is an alkylene or an alkylene group, m is 0 or 1, and Z is

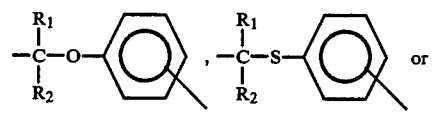

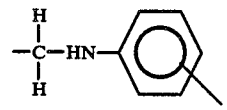

wherein $R_1$ and $R_2$, which may be the same or different, each is a hydrogen atom or an alkyl group, and the terminal carbon atom bonded to the hetero atom of Z may be bonded to either $A_1$ or $A_2$ or COOR group (in the case of m being 0); and the pharmaceutically acceptable salts thereof. These compounds have a strong inhibitory effect on thromboxane synthetase from human or bovine platelet microsomes, and are useful as therapeutically actives for inflammation, hypertension, thrombus, cerebral apoplexy and asthma.

43 Claims, No Drawings

IMIDAZOLE DERIVATIVES AND PHARMACEUTICAL USE THEREOF

BACKGROUND OF THE INVENTION

1. Field of the Invention

This invention relates to novel imidazole derivatives. More particularly, this invention relates to novel imidazole derivatives of the formula:

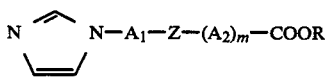

wherein R is a hydrogen atom or an alkyl group, $A_1$ and $A_2$, which may be the same or different, each is an alkylene or an alkenylene group, m is 0 or 1, and Z is

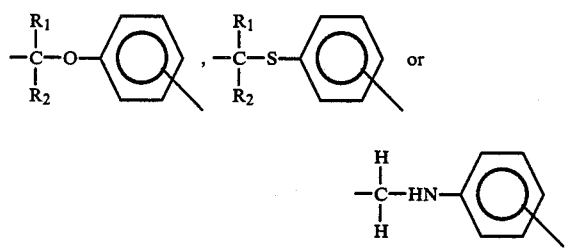

wherein $R_1$ and $R_2$, which may be the same or different, each is a hydrogen atom or an alkyl group, and the terminal carbon atom bonded to the hetero atom of Z may be bonded to $A_1$ or $A_2$ or COOR group (in the case of m being 0); and to pharmaceutical compositions containing them.

2. Description of the Prior Art

Up to now, of the compounds having an imidazole skeleton, it has been reported that imidazole, 1-alkylimidazoles, 1-benzylimidazole, 1-(2-isopropylphenyl)imidazole and their analogues possess an inhibitory action for thromboxane synthetase [*Prostaglandins,* Vol. 13, No. 4, 611- (1977), *BIOCHEMICAL AND BIOPHYSICAL RESEARCH COMMUNICATIONS,* Vol. 80, No. 1, 236- (1978)]. However, since imidazole and 1-lower alkylimidazoles of these compounds above show only very weak inhibitory effect, these compounds are hardly applicable as practically effective medicines. On the other hand, 1-benzylimidazole, 1-(2-isopropylphenyl)imidazole, 1-higher alkylimidazoles such as 1-nonylimidazole and 1-decylimidazole, and their analogues show a strong inhibitory effect as compared with the imidazole and 1-lower alkylimidazoles, but the inhibitory potency of these compounds is yet far from satisfactory one as therapeutically active agents. In addition, the action of these compounds is not a specific inhibitory action for thromboxane synthetase because of possessing both inhibitory actions for thromboxane synthetase and cyclooxygenase. Furthermore, in the case of 1-(2-isopropylphenyl)imidazole, the preparation of this compound is difficult, so that the problem of industrial application remains still unsettled.

Meanwhile, many compounds which have an imidazole skeleton and which might be considered superficially to be similar to the compounds of this invention from a chemical structural standpoint have been reported, e.g., in *J. Chem. Soc.,* 1670–(1975), *Monatsch Chem.,* Vol. 108, No. 5, 1059- (1977), *J. Med. Chem.,* Vol. 18, No. 8, 833- (1976), *J. Amer. Chem. Soc.,* Vol. 79, 4922- (1957), U.S. Pat. No. 3,541,109, French Pat. No. 7,799M, French Pat. No. 1,486,817, *Chemical Abstracts,* Vol. 71, 90,645g (1969), ibid., 83, 164,069u (1975), ibid., 88, 36,814z (1978), *J. Org. Chem.,* Vol. 22, 1323- (1975), British Pat. No. 1,148,103, etc. However, all compounds disclosed in the above literature are not reported as to whether or not they exhibit an action for thromboxane synthetase.

Therefore, research for some compounds possessing a much stronger and more specific inhibitory effect on thromboxane synthetase has been long demanded in the medical field.

As a result of extensive research and experimentation carried out for imidazole derivatives, it was found that such demand was satisfied with use of the compounds of the formula (I).

The imidazole derivatives of this invention possess a strong and specific inhibitory effect on thromboxane synthetase and are useful as therapeutically active agents for the treatment of inflammation, hypertension, thrombus, cerebral apoplexy and asthma.

SUMMARY OF THE INVENTION

Accordingly, an object of this invention is to provide compounds which exhibit a strong and specific inhibitory effect on thromboxane synthetase and which are therapeutically useful.

Another object of this invention is to provide novel imidazole derivatives possessing a pharmacological property.

Still another object of this invention is to provide the imidazole derivatives of the formula (I) or the pharmaceutically acceptable salts thereof.

Yet another object of this invention is to provide pharmaceutical compositions comprising the imidazole derivatives of the formula (I) or the pharmaceutically acceptable salts thereof.

A further object of this invention is to provide methods for the treatment of diseases such as inflammation, hypertension, thrombus, cerebral apoplexy and asthma using the imidazole derivatives of the formula (I) or the pharmaceutically acceptable salts thereof.

Other objects, features and advantages of this invention will become more apparent from the following description of the invention.

DETAILED DESCRIPTION OF THE INVENTION

The present invention provides imidazole derivatives of the formula (I):

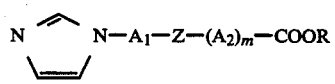

wherein R is a hydrogen atom or an alkyl group, $A_1$ and $A_2$, which may be the same or different, each is an alkylene or an alkenylene group, m is 0 or 1, and Z is

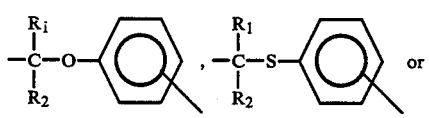

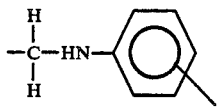

wherein $R_1$ and $R_2$, which may be the same or different, each is a hydrogen atom or an alkyl group, and the terminal carbon atom bonded to the hetero atom of Z may be bonded to $A_1$ or $A_2$ or COOR (in the case of m being 0); and the pharmaceutically acceptable salts thereof.

The term "alkyl" as used herein means a straight or branched chain alkyl group having 1 to 6 carbon atoms.

The term "alkoxyl" as used herein means a straight or branched chain alkoxyl group having 1 to 6 carbon atoms.

The term "alkylene" or "alkenylene" as used herein means straight or branched chain alkylene or alkenylene group having 1 to 8 carbon atoms unless otherwise indicated.

The term "acid residual group" as used herein means a halogen atom or an acid residual group formed from an organic or inorganic sulfonic acid.

The symbol "Y" as used herein means the carbon atom which is bonded to $R_1$ and $R_2$ of Z and which may be bonded to either $A_1$ or $A_2$.

The imidazole derivatives of the formula (I) of this invention exhibit an inhibitory action for thromboxane synthetase from human or bovine platelet microsomes. That is, the imidazole derivatives of this invention inhibit conversion of PROSTAGLANDIN $H_2$ into THROMBOXANE $B_2$ via THROMBOXANE $A_2$ which is an unstable intermediate and which is known to induce irreversible platelet aggregation and to contract smooth muscle and particularly a blood vessel muscle. [Nature, Vol. 261, No. 6, 17- (1976)]. These facts demonstrate that the imidazole derivatives of this invention inhibit the biosynthesis of thromboxane $A_2$, and are thus useful for the treatment of diseases caused by thromboxane $A_2$, such as inflammation, hypertension, thrombux, cerebral apoplexy and asthma.

The inhibitory action of the imidazole derivatives of this invention can be confirmed by determination of thromboxane $B_2$ produced by thromboxane synthetase from prostaglandin $H_2$ via thromboxane $A_2$. Furthermore, the inhibitory action of the imidazole derivatives of this invention can be confirmed by determination of the inhibitory effect on platelet aggregation caused by arachidonic acid (arachidonic acid is converted to prostaglandin $H_2$ by cyclooxygenase, and prostaglandin $H_2$ is converted to thromboxane $B_2$ via thromboxane $A_2$ which is known to induce platelet aggregation as described above).

Further still, the inhibitory action of the imidazole derivatives of this invention can be confirmed by determination of the inhibitory effect on sudden death caused by arachidonic acid.

The imidazole derivatives of this invention are characterized by the presence of the side chain having a methyl-oxy-, -thio- or -amino-phenyl moiety, which is attached at 1-position of imidazole skeleton, and which has a carboxy group or an alkoxycarbonyl group at ω-position of the side chain or on the phenyl ring (in the case that m is 0 when Y is bonded to $A_1$).

In the imidazole derivative of the formula (I) above of this invention, the potency of the inhibitory action for thromboxane synthetase varies significantly by the fact whether Y is bonded to $A_1$ or $A_2$, that is, when Y is bonded to $A_1$, $A_1$ is to have an alkylene or an alkenylene group containing one or more linear carbon atoms to provide a strong inhibitory effect, and in this case, it is most desirable that m is 0 or $A_2$ is an alkylene or an alkenylene group having 1 to 3 carbon atoms. On the other hand, when Y is bonded to $A_2$ or COOR group (in the case of m being 0), the compounds wherein the phenyl group directly attached at 1-position of the imidazole are extremely weak in the inhibitory activity on thromboxane synthetase.

The position of substitution on the phenyl ring may be in any of the o-, m- or p-position, but o- and p-substituted compounds tend to have a strong inhibitory effect on thromboxane synthetase compared with m-substituted compounds.

In the imidazole derivatives of the formula (I) above of this invention, both of ester compounds and free acid compounds possess a strong inhibitory effect on thromboxane synthetase.

Of the imidazole derivatives of the formula (I), the compounds having an alkyl group as a branched chain, also are as strong on the inhibitory effect as the corresponding compounds having a linear alkylene or alkenylene group.

Furthermore, no significant difference is found in the inhibitory effect between the alkylene compounds and alkenylene compounds, and the imidazole derivatives of the formula (I) having one or more unsaturated bonds, involve the isomers, and those isomers may be employed for this invention.

Therefore, the scope of the claimed compounds of the imidazole derivatives of this invention is set limits to the above definition.

In the compounds wherein Y is bonded to $A_1$, preferred compounds include compounds wherein $A_1$ is methylene or ethylene group and $A_2$ is an alkylene group having two and below linear carbon atoms, or m is 0, such as p-[β-(1-imidazolyl)ethoxy]cinnamic acid, 3-{p-[β-(1-imidazolyl)ethoxy]phenyl-γpropionic acid, p-[β-(1-imidazolyl)ethoxy]benzoic acid, p-[β-(1-imidazolyl)ethylamino]benzoic acid, p-[γ-(1-imidazolyl)propoxy]benzoic acid and alkyl esters of these acids. In the above preferred compounds, more preferred compounds include compounds wherein Z is an oxygen atom or a nitrogen atom and $A_1$ is a methylene group and m is 0. That is, p-[β-(1-imidazolyl)ethoxy]benzoic acid and p-[β-(1-imidazolyl)ethylamino]benzoic acid are more preferred.

In the compounds wherein Y is bonded to $A_2$ or COOR group (in case of m being 0), preferred compounds include compounds wherein $A_1$ is methylene group, m is 0 or $A_2$ is an alkylene group having three and less carbon atoms, such as o-(1-imidazolylmethyl)phenoxyacetic acid, m-(1-imidazolylmethyl)phenoxyacetic acid, p-(1-imidazolylmethyl)phenoxyacetic acid, 2-[o-(1-imidazolylmethyl)phenoxy]propionic acid, 2-[p-(1-imidazolylmethyl)phenoxy]propionic acid, α-[p-(1-imidazolylmethyl)phenoxy]isobutyric acid, α-[p-(1-imidazolylmethyl)phenylthio]isobutyric acid and alkyl esters of these acids.

In these preferred compounds, more preferred compounds include compounds wherein Z has an oxygen atom and $A_1$ is methylene group, and m is 0 or $A_2$ is an alkylene group having three and less carbon atoms. That is, p-(1-imidazolylmethyl)phenoxyacetic acid, ethyl 2-[o-(1-imidazolylmethyl)phenoxy]propionate, 2-[p-(1-imidazolylmethyl)phenoxy]propionate and α-[p-(1-imidazolylmethyl)phenoxy]isobutyric acid are more preferred.

The imidazole derivatives of the formula (I) of this invention can be prepared by the following procedures.

Of the imidazole derivatives of the formula (I), for example, the compounds of the formula (Ia):

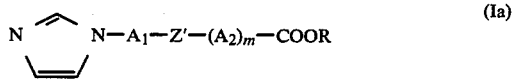

(Ia)

wherein $A_1$, $A_2$ and m have the same meanings as given above, and $Z'$ is

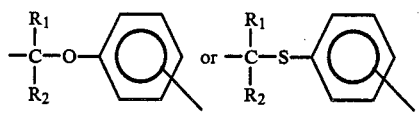

wherein $R_1$ and $R_2$ have the same meanings as given above, and the terminal carbon atom bonded to the hetero atom of $Z'$ may be bonded to $A_1$ or $A_2$ or COOR group (in case of m being 0), can be prepared by reacting imidazole of the formula (II):

(II)

with a compound of the formula (III):

(III)

wherein $A_1$, $A_2$, $Z'$ and m have the same meanings as given above, and X is an acid residual group, and $R_3$ is an alkyl group, and then, if desired, hydrolyzing the resulting product to form a compound wherein R is a hydrogen atom.

The above-described process is well known in this art, and can easily be carried out according to the procedure described in literature. That is, the N-alkylation described above in the reaction of imidazole of the formula (II) with a compound of the formula (III) can easily be carried out by dissolving or suspending a basic substance such as sodium carbonate, potassium carbonate, sodium hydride, sodium hydroxide, potassium hydroxide, a sodium alkoxide such as sodium methoxide, sodium ethoxide and the like, diisopropylethylamine, pyridine, triethylamine, etc., in an inert organic solvent, e.g., benzene, tetrahydrofuran, dioxane, toluene, xylene, acetonitrile, N,N-dimethylformamide, ethanol, butanol, etc., and to the solution or suspension, adding imidazole in an equimolar amount to the basic substance, and then heating the mixture to about room temperature to about 150° C. for about 10 minutes to about 20 hours, subsequently, adding a solution of the compound of the formula (III) in a proportion of about 1 to 0.9 mol per mol of imidazole in an inert organic solvent such as those described above to the reaction mixture, and heating the resulting mixture to about 20° to 150° C. for about 10 minutes to about 20 hours. The reaction mixture is concentrated under reduced pressure, and the residue is recrystallized or column chromatographed to obtain the desired product. If desired, the resulting product is hydrolyzed in the usual manner in an aqueous solution of an alkali to obtain the acid compound. In this process, instead of using the basic substance, the reaction can be carried out by using imidazole in an excess amount, e.g., more than twice molar amounts, of the compound of the formula (III) above. The reaction can also be carried out in the absence of any solvent, and can be carried out in the presence of a crown ether or a phase transfer catalyst such as tetrabutyl ammonium bromide, etc.

Of the imidazole derivatives of the formula (Ia), the compounds of the formula (Ia'):

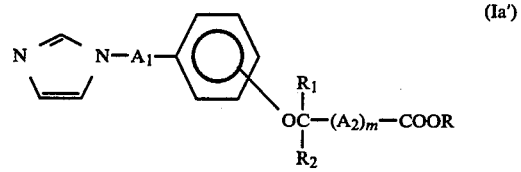

(Ia')

wherein $A_1$, $A_2$, R, $R_1$, $R_2$ and m have the same meanings as given above, can also be prepared by reacting a compound of the formula (IV):

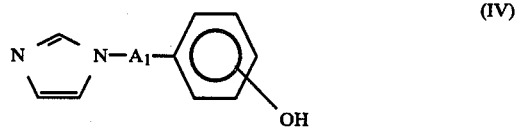

(IV)

wherein $A_1$ has the same meanings as given above, with a compound of the formula (V):

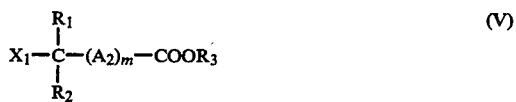

(V)

wherein $A_2$, $R_1$, $R_2$ and $R_3$ have the same meanings as given above, and $X_1$ is an acid residual group, and then, if desired, hydrolyzing the resulting compound to form a compound wherein R is a hydrogen atom.

This reaction is also well known in this art, and can be carried out according to the procedure described in literature. That is, the O-alkylation described above in the reaction of a compound of the formula (IV) with a compound of the formula (V) can easily be carried out by dissolving or suspending a basic substance such as sodium carbonate, potassium carbonate, sodium hydride, sodium hydroxide, potassium hydroxide, a sodium alkoxide such as sodium methoxide and the like, diisopropylethylamine, pyridine, triethylamine, etc., in an inert organic solvent, e.g., benzene, tetrahydrofuran, dioxane, toluene, xylene, N,N-dimethylformamide, ethanol, butanol, etc., and to the solution or suspension, adding a compound of the formula (IV) in an equimolar amount to the basic substance, and then heating the mixture to about 40° to about 150° C. for about 10 minutes to about 2 hours, subsequently, adding a solution of the compound of the formula (V) in a proportion of about 1 to 0.9 mol per mol of the compound of the formula (IV) in an inert organic solvent such as those described above to the reaction mixture, and heating the resulting mixture to about 50° to about 150° C. for about 30 minutes to about 8 hours. The reaction mixture is concentrated under reduced pressure, and the residue is recrystallized or column chromatographed to obtain the desired product. If desired, the resulting product is hydrolyzed in the usual manner in an aqueous solution of an alkali to obtain the acid compound.

In the above processes, the imidazole of the formula (II), the compound of the formula (II), the compound of the formula (V) used as starting materials are well known and can easily be prepared according to the methods disclosed in literatures.

The compound of the formula (IV) is a new compound and can be prepared by reacting imidazole of the formula (II):

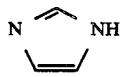
(II)

with a compound of the formula (VI):

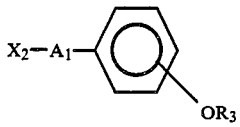
(VI)

wherein $A_1$ and $R_3$ have the same meanings as given above, and $X_2$ is an acid residual group, to obtain a compound of the formula (VII):

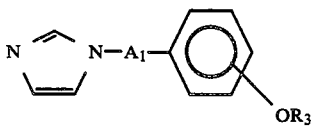
(VII)

wherein $A_1$ and $R_3$ have the same meanings as given above, and then dealkylating the resulting product to obtain a compound of the formula (IV).

The above-described process for the production of a compound of the formula (IV) can be carried out by suspending a basic substance such as sodium carbonate, potassium carbonate, sodium hydride, sodium hydroxide, potassium hydroxide, a sodium alkoxide such as sodium methoxide, sodium ethoxide and the like, diisopropylamine, pyridine, triethylamine, etc., in an inert organic solvent, e.g., benzene, tetrahydrofuran, dioxane, toluene, xylene, acetonitrile, N,N-dimethylformamide, ethanol, etc., and adding imidazole in an equimolar amount to the basic substance to the suspension, and heating the mixture to about room temperature to about 200° C. for about 10 minutes to about 20 hours, subsequently, adding a compound of the formula (VI) in a proportion of about 1 to 0.9 mol per mol of imidazole to the reaction mixture, then heating the resulting mixture to about 20° to about 150° C. for about 10 minutes to about 20 hours, concentrating the resulting reaction mixture, and then recrystallizing or column chromatographing the residue to obtain a compound of the formula (VII), and then dealkylating the compound thus-obtained using an acid such as hydrobromic acid, etc., according to the usual manner to obtain the desired compound.

Of the imidazole derivatives of the formula (I), the compounds of the formula (Ib):

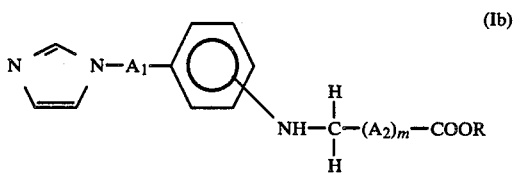
(Ib)

wherein $A_1$, $A_2$, R and m have the same meanings as given above, can be prepared by reacting a compound of the formula (VIII):

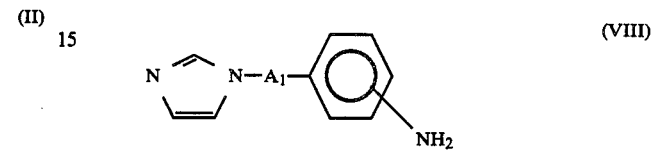
(VIII)

wherein $A_1$ has the same meanings as given above, with a compound of the formula (V'):

(V')

wherein $X_1$, $A_2$, $R_3$ and m have the same meanings as given above, and, if desired, hydrolyzing the resulting compound to form a compound wherein R is a hydrogen atom.

The above-described process for the production of a compound of the formula (Ib) can be carried out according to the procedure known per se. That is, a solution of a compound of the formula (VIII) and formic acid in an inert organic solvent such as toluene, xylene, etc., is heated under reflux for about 3 hours to 8 hours while removing the water formed. The reaction mixture is concentrated under reduced pressure, and the residue is recrystallized or column chromatographed to obtain an N-formylaniline compound. Then, the resulting compound is added to a suspension or a solution of a basic substance such as sodium hydride, a sodium alkoxide such as sodium methoxide, sodium ethoxide and the like, etc., in an equimolar amount to the N-formylaniline compound, in an inert organic solvent, e.g., benzene, dioxane, toluene, xylene, tetrahydrofuran, N,N-dimethylformamide, etc., and the mixture is heated to about 40° to about 150° C. for 10 minutes to about 3 hours. A solution of a compound of the formula (V') in an inert organic solvent such as described above is added to the reaction mixture, and the resulting mixture is heated to about 50° to about 150° for about 8 hours to about 20 hours. The reaction mixture is concentrated under reduced pressure, and the residue is purified by recrystallization or column chromatography. The compound thus-obtained is converted to the desired product by treating in the usual manner to remove the formyl group. In this process, the compound of the formula (V') used as starting material is a known compound and can be prepared according to the method disclosed in literature. The compound of the formula (VIII) used as starting material is a new compound and can be prepared by reacting imidazole of the formula (II):

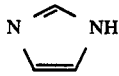 (II)

with a compound of the formula (IX):

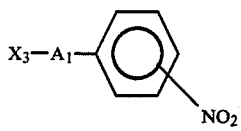 (IX)

wherein $A_1$ has the same meanings as given above and $X_3$ is an acid reisdual group, according to the reaction of imidazole with a compound of the formula (VI), and then hydrogenating the resulting compound using a catalyst such as palladium-charcoal, etc., under a pressure of 1 to 5 atms.

Of the imidazole derivatives of the formula (I), the compound of the formula (Ic):

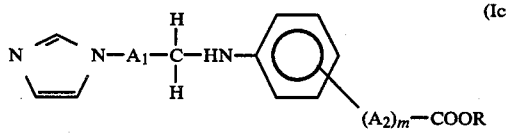 (Ic)

wherein $A_1$, $A_2$, R and m have the same meanings as given above, can be prepared by reacting imidazole of the formula (II):

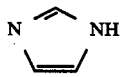 (II)

with a compound of the formula (X):

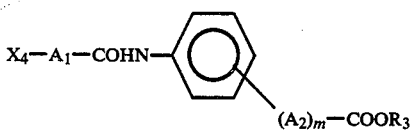 (X)

wherein $A_1$, $A_2$, m and $R_3$ have the same meanings as given above, and $X_4$ is an acid residual group, and then reducing the resulting product using a reducing agent such as sodium acetoxyborohydride, etc., to obtain a compound of the formula (Ic). This reaction is also well known, and can be easily carried out by the following procedures. That is, to a solution of a basic substance such as sodium carbonate, potassium carbonate, sodium hydride, sodium hydroxide, potassium hydroxide, a sodium alkoxide such as sodium methoxide, sodium ethoxide and the like, diisopropylethylamine, pyridine, triethylamine, etc., in an inert organic solvent, e.g., benzene, tetrahydrofuran, dioxane, toluene, xylene, N,N-dimethylformamide, ethyl alcohol, etc., is added imidazole in an equimolar amount to the basic substance, and the mixture is heated to room temperature to about 150° C. for about 10 minutes to about 3 hours. A solution of a compound of the formula (X) in a proportion of 1 to 0.9 mol per mol of the imidazole in an inert organic solvent such as those described above is then added to the reaction mixture, and the resulting mixture is heated to about 50° to about 150° C. for about 1 hour to about 5 hours. The reaction mixture is concentrated under reduced pressure, and the residue is purified by distillation or column chromatography to obtain an imidazolyl-amide compound. Then, the resulting compound is dissolved in an inert organic solvent such as tetrahydrofuran, diethyl ether, benzene, etc., and to solution is added an adequate amount of a reducing agent such as sodium acetoxyborohydride, etc., and then the mixture is heated to about 30° to about 150° C. for about 1 hour to about 5 hours. The reaction mixture is concentrated under reduced pressure, and the residue is purified by distillation or column chromatography to a compound of the formula (Ic). In this process, the compound of the formula (X) used as starting material is a new compound and can be prepared by reacting a compound of the formula (XI):

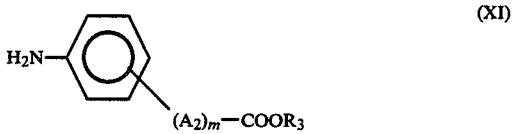 (XI)

wherein $A_2$, $R_3$ and m have the same meanings as given above, with a compound of the formula (XII):

$X_4$—$A_1$—COOH     (XII)

wherein $A_1$ and $X_4$ have the same meanings as given above, or with a reactive functional derivatives of the compound of the formula (XII), according to the usual method.

In this invention, a compound of the formula (I) wherein $A_1$ and/or $A_2$ are alkenylene groups can also be converted to the compound having an alkylene group except for the compound having sulfur atom by catalytically hydrogenating in the presence of a catalyst such as palladium-charcoal, platinum dioxide, etc., under hydrogen gas atmosphere.

The compounds of the formula (I) of this invention having a free carboxyl group or a free amine group can be converted according to the usual methods to pharmaceutically acceptable salts thereof. For example, the free-form compound of the formula (I) is dissolved in a solvent, e.g., an alcohol, water, etc., an adequate amount of hydrochloric acid or sodium hydroxide is added to the solution, the mixture is stirred at room temperature for an adequate period of time, the solvent is then distilled off, and the residue is recrystallized to obtain the salt of compound of the formula (I). Suitable examples of such pharmaceutically acceptable salts include in addition to the hydrochloric acid salt, the sulfuric acid salt, the nitric acid salt, the phosphoric acid salt, the sulfonic acid salt, the benzoic acid salt, the succinic acid salt, the tartaric acid salt, the citric acid salt, etc. On the other hand, as examples of such pharmaceutically acceptable base additional salts, in addition to the sodium salt, there are the potassium salt, the calcium salt, the magnesium salt, etc.

In the case of the salts of the compounds of the formula (I), the salt form of the compounds can be converted according to the usual methods to the free form of the compound thereof. For example, the salt form of the compound of the formula (I) is dissolved in water, then an adequate amount of hydrochloric acid or sodium hydroxide is added to solution, and the mixture is stirred at room temperature for an adequate period of time, water is removed, and the residue is distilled under reduced pressure or recrystallized from a solvent to obtain the desired compound.

Acid or base addition salts of the compounds of this invention have as high an inhibitory effect on thromboxane synthetase as the corresponding compounds having a free amino group or an acid group.

The imidazole derivatives of this invention possess a strong inhibitory effect on thromboxane synthetase, for example, 4-(1-imidazolylmethyl)phenoxyacetic acid hydrochloride produce a 50% inhibition for thromboxane synthetase from human or bovine platelet microsomes at the molar concentrations $4 \times 10^{-8}$, and are useful as therapeutically active agents for the treatment of inflammation, hypertension, thrombus, cerebral apoplexy and asthma.

The imidazole derivatives of the formula (I) and the pharmaceutically acceptable salts thereof of this invention can be administered to mammals including humans by oral, intravenous, intramuscular or intrarectal administration, and for such administration they can be formulated into pharmaceutical compositions together with conventional pharmaceutically acceptable carriers.

The compounds can be administered in various forms according to the purposed therapy. Typical dosage forms which can be used are tablets, pills, powders, liquid preparations, suspensions, emulsions, granules, capsules, suppositories and injectable preparations.

In molding the pharmaceutical composition into a tablet form, a wide variety of conventional carriers known in this art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated to make sugar-coated tablets, gelatin-coated tablets, enteric-coated tablets, film-coated tablets, or tablets coated with two or more layers.

When the pharmaceutical composition is formulated into an injectable preparation, the resulting solution and suspension are preferably sterilized, and are isotonic with respect to the blood. In formulating the pharmaceutical composition into the form of a solution or suspension, any types of diluents customarily used in the art can be used. Examples of suitable diluents ae water, ethyl alcohol, propylene glycol, ethoxyate isostearyl alcohol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, perfumes, flavors, sweeteners and other drugs.

The dosage of the compound of this invention can be about 1 mg to 1,000 mg/body by oral administration, or about 0.1 mg to 100 mg/body by parenteral administration per day for adult human in multiple doses depending upon the disease which is being treated.

This invention is further illustrated in more detail by way of the following examples wherein the melting point or the boiling point of the product obtained are uncorrected. Unless otherwise indicated, all parts, percents, ratios and the like are by weight.

REFERENCE EXAMPLE 1 p-(1-Imidazolylmethyl)phenol hydrobromide

To a suspension of 5.21 g of 50% sodium hydride in 100 ml of dry dimethylformamide was added slowly 7.39 g of imidazole at room temperature, and the mixture was stirred for 20 minutes. A solution of 20 g of p-methoxybenzyl chloride in 30 ml of dry dimethylformamide was added to the mixture at room temperature over a period of 1 hour, and then the reaction mixture was stirred for 18 hours at 50° C. After removal of the solvent under reduced pressure, 100 ml of dichloromethane was added to the residual oil and the mixture was washed with water and dried over anhydrous magnesium sulfate. The solvent was evaporated and the residual solid was recrystallized from diethyl ether-ligroin to give 14.7 g of p-(1-imidazolylmethyl)anisole as colorless platelets. Then a solution of 14.7 g of p-(1-imidazolylmethyl)anisole in 50 ml of 47% hydrobromic acid was refluxed for 3 hours. After concentration under reduced pressure, the residual solid was recrystallized from ethanol-diethyl ether to give 18.4 g of p-(1-imidazolylmethyl)phenol hydrobromide as colorless platelets. M.P.: 189°–190° C.

NMR Spectrum (DMSO-$D_6$): $\delta$5.49 (s, 2H), 6.97 (d, 2H), 7.49 (d, 2H), 7.88 (t, 1H), 7.99 (t, 1H), and 9.49 (br-s, 1H).

Elemental Analysis as $C_{10}H_{10}N_2O \cdot HBr$: Calcd. C, 47.08; H, 4.35; N, 10.98. Found C, 47.12; H, 4.22; N, 10.92.

REFERENCE EXAMPLE 2 p-(1-Imidazolylmethyl)aniline

A mixture of 13.6 g of imidazole, 43.2 g of p-bromomethylnitrobenzene and 55.2 g of anhydrous potassium carbonate in 300 ml of dry toluene was refluxed for 18 hours. After concentration under reduced pressure, 200 ml of dichloromethane was added to the residue and insoluble salts were filtered off. The filtrate was evaporated and the residue was chromatographed on silica gel using dichloromethane-ethanol (20:1 by volume) to give 27.9 g of p-(1-imidazolylmethyl)nitrobenzene as pale yellow platelets. Then, a solution of 2.0 g of this product in 50 ml of ethanol was hydrogenated over 0.2 g of palladium on carbon at room temperature under a hydrogen pressure of 4 atms. After filtration and evaporation, the residual solid was recrystallized from ethanol-diethyl ether-petroleum ether to give 1.4 g of p-(1-imidazolylmethyl)aniline as colorless needles. M.P.: 134°–137° C.

IR-Absorption Spectrum (KBr): $\nu$NH 3300 cm$^{-1}$ and 3450 cm$^{-1}$.

NMR Spectrum (CDCl$_3$): $\delta$3.96 (br, 2H), 5.01 (s, 2H), 6.70 (d, 2H), 6.95 (t, 1H), 7.04 (d, 2H), 7.12 (m, 1H), and 7.59 (br-s, 1H).

Elemental Analysis as $C_{10}H_{11}N_3$: Calcd. C, 69.34; H, 6.40; N, 24.26. Found C, 69.23; H, 6.41; N, 24.12.

EXAMPLE 1

Ethyl 2-[o-(1-imidazolylmethyl)phenoxy]propionate

To a suspension of 5.7 g of 50% sodium hydride in 200 ml of dry dimethylformamide was added slowly 8.0 g of imidazole at room temperature, and then the mixture was stirred for 30 minutes. A solution of 34.1 g of ethyl 2-(o-bromomethylphenoxy)propionate in 50 ml of dry dimethylformamide was added to the mixture at room temperature over a period of 1 hour, and then the reaction mixture was stirred at the same temperature for 1 hour. After removal of the solvent under vacuum, 150 ml of dichloromethane was added to the residual oil and the solution was washed with water and dried over anhydrous magnesium sulfate. The solvent was evaporated and the residual oil was chromatographed on silica gel using dichloromethane-ethanol (20:1 by volume) to give 15 g of ethyl 2-[o-(1-imidazolylmethyl)-phenoxy]propionate as colorless needles. M.P.: 84°–85° C.

IR-Absorption Spectrum (KBr): $\nu$CO 1740 cm$^{-1}$.

NMR Spectrum (CDCl$_3$): $\delta$1.24 (t, 3H), 1.64 (d, 3H), 4.27 (q, 2H), 4.90 (q, 1H), 5.26 (s, 2H), 6.8–7.45 (m, 6H), and 7.69 (br-s, 1H).

Elemental Analysis as $C_{15}H_{18}O_3N_2$: Calcd. C, 65.67; H, 6.61; N, 10.21. Found C, 65.68; H, 6.75; N, 10.01.

The following compounds were prepared in a similar manner to the procedure described above.

TABLE 1

$$\text{N} \diagup\text{NH} + \text{X}-\text{A}_1-\text{Z}-(\text{A}_2)_m-\text{COOEt} \longrightarrow \text{N} \diagup\text{N}-\text{A}_1-\text{Z}-(\text{A}_2)_m-\text{COOEt}$$

| X | A$_1$ | m | A$_2$ | Z | Yield (%) | M.P. (°C.) | IR (cm$^{-1}$) | NMR (CDCl$_3$) $\delta$ |
|---|---|---|---|---|---|---|---|---|
| Br | CH$_3$ | 0 | — | (2-substituted phenyl)–O–CH$_2$ | 36 | 61–62 | (KBr) $\nu$CO 1740 | 1.32(t,3H), 4.36(q,2H), 4.71(s,2H), 5.26(s,2H), 6.8–7.5(m,6H), and 7.72(br-s,1H). |
| Br | CH$_2$ | 0 | — | (3-substituted phenyl)–O–CH$_2$ | 38 | oil | (neat) $\nu$CO 1755 | 1.26(t,3H), 4.24(q,2H), 4.55(s,2H), 5.04(s,2H), and 6.6–7.5(m,7H). |
| Br | CH$_2$ | 0 | — | (4-substituted phenyl)–O–CH$_2$ | 55 | oil | (neat) $\nu$CO 1750 | 1.27(t,3H), 4.24(q,2H), 4.58(s,2H), 5.00(s,2H), 6.7–7.1(m,6H), and 7.45(br-s,1H). |
| Br | CH$_2$ | 0 | — | (4-substituted phenyl)–O–CH(Me) | 45 | oil | (neat) $\nu$CO 1740 | 1.21(t,3H), 1.59(d,3H), 4.19(q,2H), 4.70(q,1H), 4.96(s,2H), 6.7–7.1(m,6H), and 7.44(br-s,1H). |
| Br | CH$_2$ | 0 | — | (4-substituted phenyl)–O–C(Me)$_2$ | 60 | oil | (neat) $\nu$CO 1725 | 1.25(t,3H), 1.61(s,6H), 4.29(q,2H), 5.10(s,2H), 6.8–7.3(m,6H), and 7.59(br-s,1H). |
| Br | CH$_2$ | 0 | — | CH$_2$–O–(4-substituted phenyl) | 58 | 96–97 | (KBr) $\nu$CO 1700 | 1.40(t,3H), 4.2–4.6(m,6H), 6.99(d,2H), 7.17(br-s,2H), 7.72(br-s,1H), and 8.12(d,2H). |
| Br | CH$_2$ | 1 | CH=CH | CH$_2$–O–(4-substituted phenyl) | 55 | 89–90 | (KBr) $\nu$CO 1705 $\nu$C=C 1635 | 1.30(t,3H), 4.1–4.4(m,6H), 6.24(d,1H), 6.79(d,2H), 6.95–7.05(m,2H), and 7.3–7.65(m,4H). |
| Br | CH$_2$ | 1 | (CH$_2$)$_2$ | CH$_2$–O–(4-substituted phenyl) | 60 | oil | (neat) $\nu$CO 1730 | 1.20(t,3H), 2.45–2.65(m,2H), 2.80–3.0(m,2H), 4.10(q,2H), 4.05–4.40(m,4H), 6.74(d,2H), 6.95–7.05(m,2H), 7.04(d,2H), and 7.52(br-s,1H). |
| Br | CH$_2$ | 0 | — | (4-substituted phenyl)–S–C(Me)$_2$ | 60 | oil | (neat) $\nu$CO 1720 | 1.21(t,3H), 1.48(s,6H), 4.16(q,2H), 5.19(s,2H), 6.97(br-s,1H), 7.05–7.25(m,3H), and 7.45–7.65(m,3H). |
| Br | (CH$_2$)$_2$ | 0 | — | CH$_2$–O–(4-substituted phenyl) | 60 | oil | (neat) $\nu$CO 1700 | 1.38(t,3H), 2.25(m,2H), 3.98(t,2H), 4.20(t,2H), 4.36(q,2H), 6.8–7.1(m,4H), 7.50(br-s,1H), and 8.00(d,2H). |

EXAMPLE 2

Ethyl 4-[p-(1-imidazolylmethyl)phenoxy]butyrate 5.0 g of p-(1-imidazolylmethyl)phenol hydrobromide prepared as described in Reference Example 1 was added slowly to a suspension of 1.88 g of 50% sodium hydride in 100 ml of dry dimethylformamide at room temperature, and then the mixture was warmed to 45° C. A solution of 3.82 g of ethyl 4-bromobutyrate in 30 ml of dry dimethylformamide was added to the mixture over a period of 30 minutes at 45° C., and then the reaction mixture was stirred for 17 hours at the same temperature. After removal of the solvent, the residual oil was diluted with 100 ml of dichloromethane, washed with water, and dried over anhydrous magnesium sulfate. The solvent was evaporated and the residue was chromatographed on silica gel using dichloromethane-ethanol (20:1 by volume) to give 3.43 g of ethyl 4-p-(1-imidazolylmethyl)phenoxybutyrate as a colorless oil.

IR-Absorption Spectrum (neat): $\nu$CO 1725 cm$^{-1}$.

NMR Spectrum (CDCl$_3$): $\delta$1.26 (t, 3H), 2.18 (m, 2H), 2.45–2.65 (m, 2H), 4.05 (t, 2H), 4.20 (q, 2H), 5.09 (s, 2H), 6.85–7.3 (m, 6H), and 7.61 (br-s, 1H).

Elemental Analysis as $C_{16}H_{20}O_3R_2$: Calcd. C, 66.64; H, 6.99; N, 9.72. Found C, 66.38; H, 7.20; N, 9.43.

EXAMPLE 3

Ethyl p-[$\beta$-(1-imidazolyl)ethylamino]benzoic acid hydrochloride

To a suspension of 2.4 g of 50% sodium hydride in 100 ml of dry dimethylformamide was added slowly 3.4 g of imidazole at room temperature, and the mixture was heated to 80° C. A solution of 12.1 g of ethyl p-chloroacetylaminobenzoate in 45 ml of dry dimethylformamide was added to the mixture over a period of 30 minutes at 80° C., and then the reaction mixture was heated at 100° C. for 1.5 hours. After removal of the solvent under reduced pressure, the residue was dissolved in chloroform and washed with water and dried over anhydrous magnesium sulfate. The solvent was evaporated and the residual solid was recrystallized from ethanol-n-hexane to give 10.5 g of ethyl p-(1-imidazolyl)acetylaminobenzoate as colorless needles. M.P.: 185°–187° C.

IR-Absorption Spectrum (KBr): $\nu$CO 1700 cm$^{-1}$.

NMR Spectrum (DMSO-D$_6$): $\delta$1.29 (t, 3H), 4.29 (q, 2H), 4.93 (s, 2H), 6.89 (br-s, 1H), 7.13 (br-s, 1H), 7.62 (br-s, 1H), 7.70 (d, 2H), 7.91 (d, 2H), and 10.59 (br-s, 1H).

Elemental Analysis as $C_{14}H_{15}O_3N_3$: Calcd. C, 61.53; H, 5.53; N, 15.38. Found C, 61.52; H, 5.59; N, 15.26.

Then, a suspension of 7.2 g of ethyl p-(1-imidazolyl)acetylaminobenzoate and 12.7 g of sodium acetoxyborohydride in 200 ml of dry tetrahydrofuran was stirred at room temperature for 1 hour and then refluxed for 5 hours. After evaporation under reduced pressure, 50 ml of water was added in small portions to the residue to decompose the excess of sodium acetoxyborohydride and the complex, and then the aqueous solution was extracted with chloroform. The chloroform extract was dried over anhydrous magnesium sulfate and saturated with dry hydrogen chloride gas at room temperature, followed by allowing to stand for 1 hour. Then, the solvent was evaporated and the residual solid was recrystallized from ethanol-diethyl ether to give 4.5 g of ethyl p-[$\beta$-(1-imidazolyl)ethylamino]benzoate hydrochloride as colorless leaflets. M.P.: 166°–168° C.

IR-Absorption Spectrum (KBr): $\nu$CO 1705 cm$^{-1}$; $\nu$NH 3280 cm$^{-1}$.

NMR Spectrum (DMSO-D$_6$): $\delta$1.27 (t, 3H), 3.64 (t, 2H), 4.22 (q, 2H), 4.46 (t, 2H), 5.4–5.9 (br, 2H), 6.65 (d, 2H), 7.63 (br-s, 1H), 7.65 (d, 2H), 7.84 (br-s, 1H), and 9.26 (br-s, 1H).

Elemental Analysis as $C_{14}H_{17}O_2N_3 \cdot HCl \cdot \frac{1}{4}H_2O$: Calcd. C, 56.00; H, 6.21; N, 14.00. Found C, 55.91; H, 6.17; N, 14.05.

Then, a solution of 1.0 g of ethyl p-[$\beta$-(1-imidazolyl)ethylamino]benzoate hydrochloride and 1.0 g of sodium hydroxide in 30 ml of methanol-water (1:2 by volume) was stirred for 2.5 hours at room temperature. After concentration under reduced pressure, the residue was acidified with 6N hydrochloric acid to pH 1, and then concentrated under reduced pressure. To the residue was added 20 ml of tert-butanol and evaporated under reduced pressure to remove the excess of hydrochloric acid completely. The residual solid was dissolved in ethanol, the insoluble salts were filtered off, and then the filtrate was evaporated under reduced pressure. The residual solid was recrystallized from ethanol-diethyl ether to give 0.65 g of p-[$\beta$-(1-imidazolyl)ethylamino]benzoic acid hydrochloride as colorless needles. M.P.: 222° to 224° C. (dec.).

IR-Absorption Spectrum (KBr): $\nu$CO 1665 cm$^{-1}$; $\nu$NH 3240 cm$^{-1}$.

NMR Spectrum (DMSO-D$_6$): $\delta$3.5–3.8 (m, 2H), 4.25–4.6 (m, 2H), 6.62 (d, 2H), 7.4–8.0 (m, 5H), and 9.22 (br-s, 1H).

Elemental Analysis as $C_{12}H_{13}O_2N_3 \cdot HCl$: Calcd. C, 53.83; H, 5.27; N, 15.70. Found C, 53.59; H, 5.46; N, 15.46.

EXAMPLE 4

N-[p-(1-Imidazolylmethyl)phenyl]alanine ethyl ester dihydrochloride

In a 200 ml round-bottom flask is placed a solution of 8.0 g of p-(1-imidazolylmethyl)aniline prepared as described in Reference Example 3, and 30 ml of formic acid in 80 ml of toluene. The flask was fitted with a water separator, and the solution was refluxed for 4 hours. After concentration under reduced pressure, the residual solid was recrystallized from ethanol-diethyl ether to give 6.4 g of p-(1-imidazolylmethyl)-N-formylaniline as colorless prisms. M.P.: 121°–123° C. To a suspension of 0.48 g of 50% sodium hydride in 50 ml of dry dimethylformamide was added 2.01 g of the formylaniline and mixture was heated to 100° C. A solution of 1.81 g of ethyl $\alpha$-bromopropionate in 30 ml of dry dimethylformamide was added to the mixture and the reaction mixture was heated at 100° C. for 16 hours. After removal of the solvent under reduced pressure, 50 ml of dichloromethane was added to the residue, and the solution was washed with water and dried over anhydrous magnesium sulfate. The solvent was evaporated and the residue was chromatographed on silica gel using dichloromethane-ethanol (20:1 by volume) to give 1.58 g of N-formyl-N-[p-(1-imidazolylmethyl)phenyl]alanine ethyl ester as a pale brown oil. Then, a solution of 1.58 g of the resulting ester and 5 ml of concentrated hydrochloric acid in 50 ml of ethanol was stirred for 40 hours at room temperature. After concentration under reduced pressure, the residual solid was recrystallized from ethanol-diethyl ether to give 1.18 g of N-[p-(1- imidazolylmethyl)phenyl]alanine ethyl ester dihydrochloride as pale yellow crystals. M.P.: 154°–159° C.

IR-Absorption Spectrum (KBr): $\nu$CO 1720 cm$^{-1}$.

NMR Spectrum (DMSO-D$_6$): δ1.13 (t, 3H), 1.39 (d, 3H), 3.95–4.25 (m, 3H), 5.29 (s, 2H), 5.85–6.40 (br, 3H), 6.68 (d, 2H), 7.22 (d, 2H), 7.60 (m, 1H), 7.73 (m, 1H), and 9.33 (m, 1H).

Elemental Analysis as C$_{15}$H$_{19}$O$_2$N$_3$.2HCl: Calcd. C, 52.03; H, 6.11; N, 12.14. Found C, 51.77; H, 6.22; N, 12.15.

EXAMPLE 5

N-[p-(1-Imidazolylmethyl)phenyl]glycine ethyl ester dihydrochloride

In the same procedure as described in Example 4, N-[p-(1-imidazolylmethyl)phenyl]glycine ethyl ester dihydrochloride was prepared from p-(1-imidazolylmethyl)aniline which was prepared as described in Reference Example 2, and ethyl bromoacetate. M.P.: 156°–159° C. (decomp.) (pale yellow prisms; recrystallized from ethanol-diethyl ether).

IR-Absorption Spectrum (KBr): $\nu$CO 1740 cm$^{-1}$.

NMR Spectrum (DMSO-D$_6$): δ1.17 (t, 3H), 3.92 (s, 2H), 4.10 (q, 2H), 5.27 (s, 2H), 6.62 (d, 2H), 7.0–8.0 (m, 7H), and 9.35 (m, 1H).

Elemental Analysis as C$_{14}$H$_{19}$O$_2$N$_3$Cl$_2$: Calcd. C, 50.61; H, 5.76; N, 12.65. Found C, 50.33; H, 5.78; N, 12.51.

EXAMPLE 6 p-(1-Imidazolylmethyl)phenoxyacetic acid hydrochloride monohydrate

A solution of 2.3 g of ethyl p-(1-imidazolylmethyl)-phenoxyacetate prepared as described in Example 1, and 0.45 g of sodium hydroxide in 30 ml of methanol-water (1:2 by volume) was stirred for 30 minutes at room temperature. After concentration under reduced pressure, the residue was acidified with 6N hydrochloric acid to pH 11 and then concentrated under reduced pressure. To the residue was added 20 ml of tert-butanol, and evaporated under reduced pressure to remove the excess of hydrochloric acid completely. The residual solid was dissolved in ethanol and the insoluble salts were filtered off. The filtrate was evaporated and a small amount of water was added to the residue, and the resulting crystals were recrystallized from ethanol-diethyl ether-water (a small amount) to give 1.5 g of p-(1-imidazolylmethyl)phenoxyacetic acid hydrochloride monohydrate as colorless needles. M.P.: 92°–96° C.

IR-Absorption Spectrum (KBr): $\nu$CO 1755 cm$^{-1}$.

NMR Spectrum (DMSO-D$_6$): δ4.67 (s, 2H), 5.40 (s, 2H), 5.6–6.1 (br, 4H), 6.88 (d, 2H), 7.38 (d, 2H), 7.60 (t, 1H), 7.75 (t, 1H), and 9.45 (br-s, 1H).

Elemental Analysis as C$_{12}$H$_{12}$O$_3$N$_2$.HCl.H$_2$O: Calcd. C, 50.27; H, 5.27; N, 9.73. Found C, 50.26; H, 5.18; N, 9.74.

The following compounds were also prepared in a similar manner to the procedure described above.

TABLE 2

$$\text{N} \diagup\!\!\diagdown \text{N}-A_1-Z-(A_2)_m-COOH \cdot HCl$$

| A$_1$ | m | A$_2$ | Z | Yield (%) | M.P. (° C.) | IR (cm$^{-1}$) | NMR (DMSO-D$_6$) δ |
|---|---|---|---|---|---|---|---|
| CH$_2$ | 0 | — | (2-substituted phenyl)–O–CH$_2$– | 82 | 167–169 | (KBr) $\nu$CO 1745 | 4.89(s,2H), 5.52(s,2H), 7.0–7.7(m,4H), 7.75(t,1H), 7.92(t,1H), 9.35(br-s,1H), and 9.0–10.4(br,2H) |
| CH$_2$ | 0 | — | (3-substituted phenyl)–O–CH$_2$– | 75 | 173–175 | (KBr) $\nu$CO 1740 | 4.67(s,2H), 5.41(s,2H), 6.75–7.40(m,4H), 7.63(t, 1H), 7.79(t,1H), 9.45(br-s,1H), and 10.0–14.0 (br,2H) |
| CH$_2$ | 0 | — | (2-substituted phenyl)–O–CH(Me)– | 80 | 172–174 | (KBr) $\nu$CO 1735 | 1.58(d,3H), 5.12(q,1H), 5.55(s,2H), 7.0–7.7(m, 4H), 7.76(br-s,1H), 7.85(br-s,1H), and 9.32(br-s,1H) |
| CH$_2$ | 0 | — | (4-substituted phenyl)–O–CH(Me)– | 74 | 155–158 | (KBr) $\nu$CO 1725 | 1.50(d,3H), 4.85(q,1H), 5.36(s,2H), 6.86(d,2H), 7.37(d,2H), 7.60(br-s,1H), 7.75(br-s,1H), and 9.35(br-s,1H) |
| CH$_2$ | 0 | — | (4-substituted phenyl)–O–C(Me)(Me)– | 75 | 174–177 | (KBr) $\nu$CO 1730 | 1.53(s,6H), 5.51(s,2H), 6.95(d,2H), 7.50(d,2H), 7.79(t,1H), 7.95(t,1H), 9.48(br-s, 1H), and 12–13(br,2H) |

TABLE 2-continued

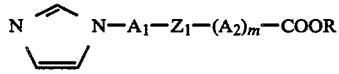

| $A_1$ | m | $A_2$ | Z | Yield (%) | M.P. (°C.) | IR (cm$^{-1}$) | NMR (DMSO-D$_6$) δ |
|---|---|---|---|---|---|---|---|
| CH$_2$ | 1 | (CH$_2$)$_2$ | 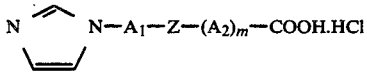 | 70 | 181–183 | (KBr) νCO 1740 | 1.85–2.15(m,2H), 2.45(t,2H), 4.06(t,2H), 5.50(s,2H), 7.06(d,2H), 7.54(d,2H), 7.79(t,1H), 7.92(t,1H), and 9.50(m,1H) |
| CH$_2$ | 1 | CH=CH | 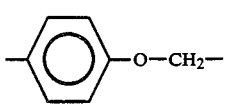 | 80 | 214–217 | (KBr) νCO 1710 νC=C 1640 | 4.35–4.80(m,4H), 6.38(d,1H), 6.96(d,2H), 7.50(d,1H), 7.59(d,2H), 7.64(t,1H), 7.84(t,1H), 9.28(br-s,1H), and 9.5–12.5(br,2H) |
| CH$_2$ | 1 | (CH$_2$)$_2$ | 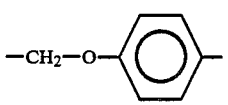 | 75 | 184–186 | (KBr) νCO 1720 | 2.35–2.65(m,2H), 2.65–2.95(m,2H), 4.25–4.50(m,2H), 4.50–4.80(m,2H), 6.80(d,2H), 7.08(d,2H), 7.63(t,1H), 7.81(t,1H), and 9.31(t,1H) |
| CH$_2$ | 0 | — | 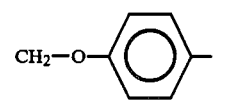 | 90 | 230–235 | (KBr) νCO 1675 | 4.4–4.6(m,2H), 4.6–4.8(m,2H), 7.01(d,2H), 7.67 (t,1H), 7.85(d,2H), 7.86(t,1H), and 9.30(br-s,1H) |
| (CH$_2$)$_2$ | 0 | — | 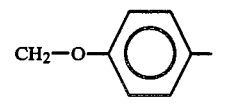 | 80 | 192–193 | (KBr) νCO 1700 | 2.35(m,2H), 4.12(t,2H), 4.45(t,2H), 6.95(d,2H), 7.65–8.0(m,4H), and 9.34(br-s,1H) |
| CH$_2$ | 0 | — | 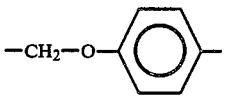 | 75 | 169–171 | (KBr) νCO 1710 | 1.38(s,6H), 5.61(s,2H), 7.53(s,4H), 7.81(m,1H), 7.95(m,1H), and 9.52(m,1H) |

While the invention has been described in detail and with reference to specific embodiments thereof, it will be apparent to one skilled in the art that various changes and modifications can be made therein without departing from the spirit and scope thereof.

What is claimed is:

1. An imidazole derivative of the formula:

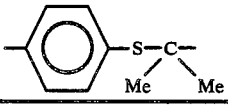

wherein R is a hydrogen atom or an alkyl group having 1 to 6 carbon atoms, A$_1$ and A$_2$, which may be the same or different, each is an alkylene group or an alkenylene group having 1 to 8 carbon atoms, m is 0 or 1, and Z is

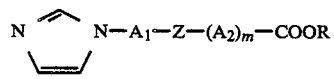

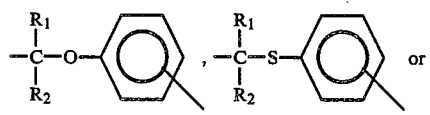

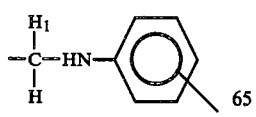

wherein R$_1$ and R$_2$, which may be the same or different, each is a hydrogen atom or an alkyl group having 1 to 6 carbon atoms, and the terminal carbon atom bonded to the hetero atom of Z may be bonded to A$_1$ or A$_2$ or COOR group (in case of m being 0); and pharmaceutically acceptable salts thereof.

2. The compound as claimed in claim 1 of the formula:

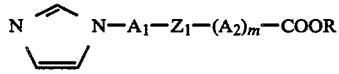

wherein Z is 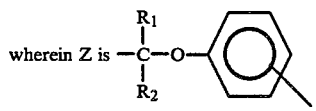

wherein R$_1$ and R$_2$ have the same meanings as given above, and the terminal carbon atom bonded to the hetero atom of Z may be bonded to A$_1$ to A$_2$ or COOR group (in case of m being 0), and A$_1$, A$_2$, m and R have the same meanings as given above; and the pharmaceutically acceptable salt thereof.

3. The compound as claimed in claim 2 of the formula:

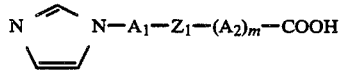

wherein $A_1$, $A_2$, $Z_1$ and m have the same meanings as given above.

4. The compound as claimed in claim 2 of the formula:

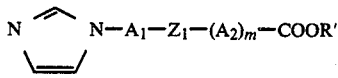

wherein $A_1$, $A_2$, $Z_1$ and m have the same meanings as given above and R' is an alkyl group.

5. The compound as claimed in claim 1 of the formula:

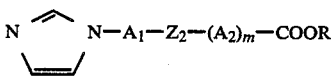

wherein $A_1$, $A_2$, m and R have the same meanings as given above and $Z_2$ is

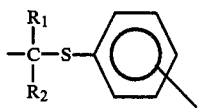

wherein $R_1$ and $R_2$ have the same meanings as given above, and the terminal carbon atom bonded to the hetero atom of Z may be bonded to $A_1$ or $A_2$ or COOR group (in case of m being 0).

6. The compound as claimed in claim 5 of the formula:

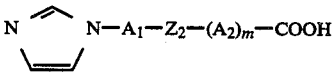

wherein $A_1$, $A_2$, $Z_2$ and m have the same meanings as given above.

7. The compound as claimed in claim 5 of the formula:

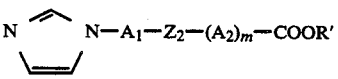

wherein $A_1$, $A_2$, $Z_2$ and m have the same meanings as given above and R' is an alkyl group.

8. The compound as claimed in claim 1 of the formula:

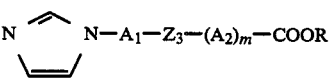

wherein $A_1$, $A_2$, m and R have the same meanings as given above and $Z_3$ is

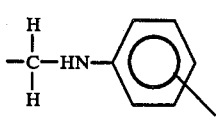

wherein the methylene group bonded to the amino group of Z may be bonded to either $A_1$ or $A_2$ or COOR group (in the case of m being 0); and the pharmaceutically acceptable salt thereof.

9. The compound as claimed in claim 8 of the formula:

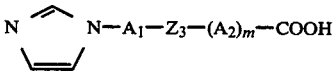

wherein $A_1$, $A_2$, $Z_3$ and m have the same meanings as given above.

10. The compound as claimed in claim 8 of the formula:

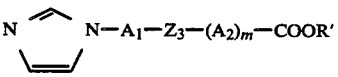

wherein $A_1$, $A_2$, $Z_3$ and m have the same meanings as given above and R' is an alkyl group.

11. The compound as claimed in claim 3 of the formula:

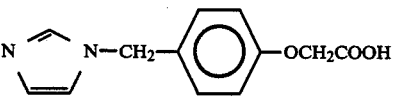

12. The compound as claimed in claim 3 of the formula:

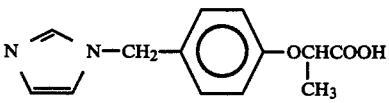

13. The compound as claimed in claim 3 of the formula:

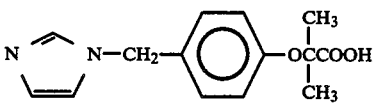

14. The compound as claimed in claim 3 of the formula:

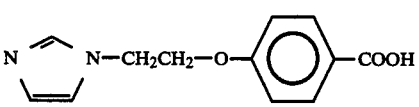

15. The compound as claimed in claim 3 of the formula:

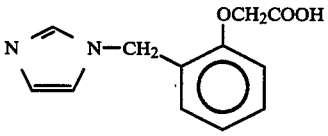

16. The compound as claimed in claim 3 of the formula:

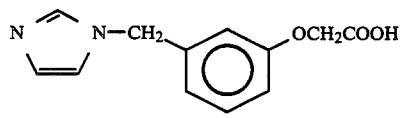

17. The compound as claimed in claim 3 of the formula:

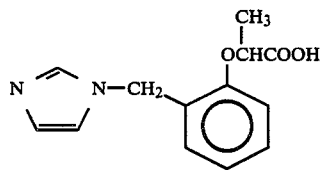

18. The compound as claimed in claim 3 of the formula:

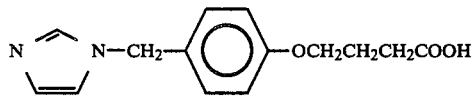

19. The compound as claimed in claim 3 of the formula:

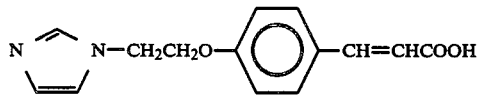

20. The compound as claimed in claim 3 of the formula:

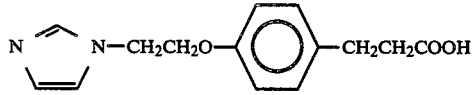

21. The compound as claimed in claim 3 of the formula:

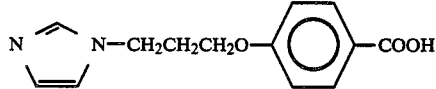

22. The compound as claimed in claim 4 of the formula:

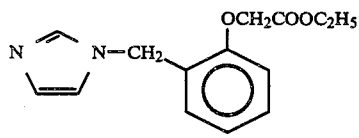

23. The compound as claimed in claim 4 of the formula:

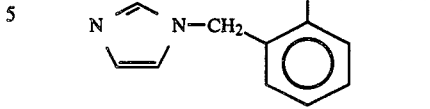

24. The compound as claimed in claim 4 of the formula:

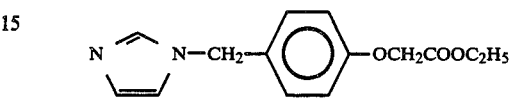

25. The compound as claimed in claim 4 of the formula:

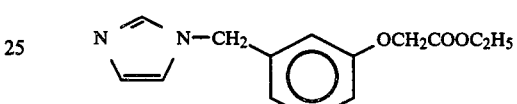

26. The compound as claimed in claim 4 of the formula:

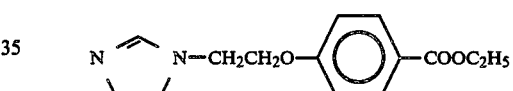

27. The compound as claimed in claim 4 of the formula:

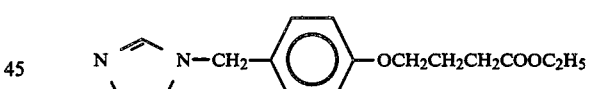

28. The compound as claimed in claim 4 of the formula:

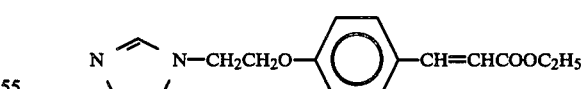

29. The compound as claimed in claim 4 of the formula:

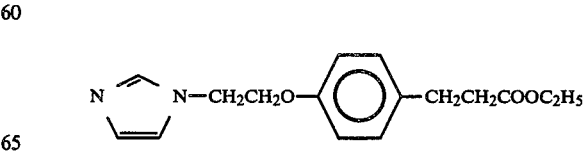

30. The compound as claimed in claim 4 of the formula:

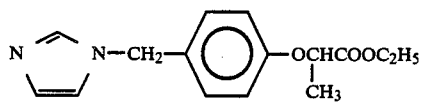

31. The compound as claimed in claim 4 of the formula:

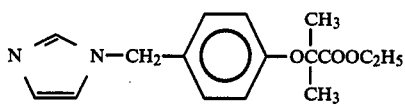

32. The compound as claimed in claim 4 of the formula:

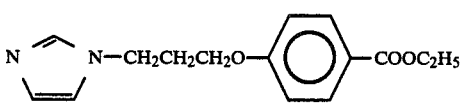

33. The compound as claimed in claim 6 of the formula:

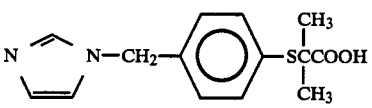

34. The compound as claimed in claim 7 of the formula:

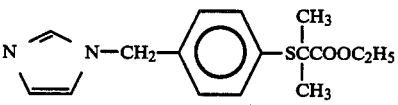

35. The compound as claimed in claim in claim 9 of the formula:

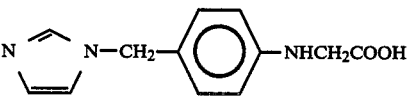

36. The compound as claimed in claim 10 of the formula:

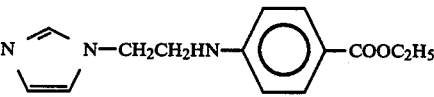

37. The compound as claimed in claim 10 of the formula:

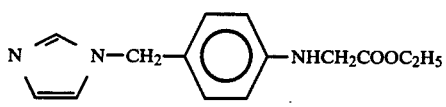

38. A pharmaceutical composition for oral administration for the treatment of inflammation, hypertension, thrombus, cerebral apoplexy, or asthma, which contains the compound of claim 1 in an amount suitable for providing a dosage of about 1 to about 1,000 mg per day.

39. A pharmaceutical composition for parenteral administration for the treatment of inflammation, hypertension, thrombus, cerebral apoplexy, or asthma, which contains the compound of claim 1 in an amount suitable for providing a dosage of about 0.1 to about 100 mg per day.

40. A method of alleviating inflammation, hypertension, thrombus, cerebral apoplexy, or asthma in mammals which comprises administering a therapeutically effective amount of at least one imidazole derivative as claimed in claim 1.

41. The compound as claimed in claims 2, 5 or 8: wherein $A_1$ is an alkylene group having 1 or 2 carbon atoms, $A_2$ is an alkylene group having 1 to 3 carbon atoms or an alkenylene group having 2 or 3 carbon atoms, and the total number of atoms in $A_1$ and $A_2$ is 2 to 4.

42. A compound selected from the group consisting of an imidazole derivative of the formula:

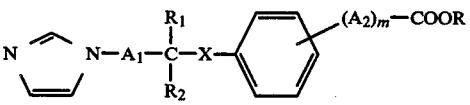

wherein R is a hydrogen atom or an alkyl group having 1 to 6 carbon atoms, each of $A_1$ and $A_2$, which may be the same or different, are alkylene having 1 to 8 carbon atoms, m is 0 or 1, X is oxygen or sulfur, and each of $R_1$ and $R_2$, which may be the same or different, is a hydrogen atom or an alkyl group having 1 to 6 carbon atoms; and the pharmaceutically acceptable salts thereof.

43. A compound of the formula:

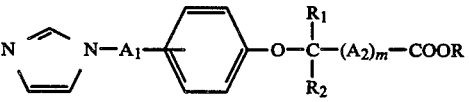

or a pharmaceutically acceptable salt thereof, wherein:
R is hydrogen or $C_1$-$C_6$ alkyl;
$R^1$ and $R^2$, which may be the same or different, each is hydrogen or $C_1$-$C_6$ alkyl;
$A_1$ and $A_2$ are the same or different and are $C_1$-$C_8$ alkylene; and
m is 0 or 1.

* * * * *